United States Patent
Sakaguchi et al.

(10) Patent No.: US 6,468,500 B1
(45) Date of Patent: Oct. 22, 2002

(54) ALUMINOSILICATE

(75) Inventors: Mikio Sakaguchi, Wakayama (JP);
Takanori Kotera, Wakayama (JP);
Masaharu Jyono, Wakayama (JP);
Ichiro Sakamoto, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/530,367

(22) PCT Filed: Oct. 26, 1998

(86) PCT No.: PCT/JP98/04852
§ 371 (c)(1),
(2), (4) Date: Apr. 28, 2000

(87) PCT Pub. No.: WO99/23033
PCT Pub. Date: May 14, 1999

(30) Foreign Application Priority Data

Oct. 31, 1997 (JP) .............................................. 9-300769

(51) Int. Cl.[7] .......................... C01B 33/26; C01B 39/02
(52) U.S. Cl. ....................... 423/700; 423/700; 423/716; 423/328.1; 423/328.2; 423/DIG. 32; 510/507; 510/532; 106/3
(58) Field of Search ................................. 423/700, 716, 423/328.1, 328.2, DIG. 32; 510/507, 532; 106/3

(56) References Cited

U.S. PATENT DOCUMENTS 3,674,709 A * 7/1972 Barrer et al.
4,020,147 A * 4/1977 Shidlovsky et al.
4,717,560 A 1/1988 Vaughan
4,954,468 A 9/1990 Wason
5,340,506 A * 8/1994 Koyama

FOREIGN PATENT DOCUMENTS

EP 0592256 4/1994
JP 04342414 A * 11/1992

OTHER PUBLICATIONS

Barrer et al., "The Hydrothermal Chemistry of Silicates. Part II. Synthetic Crystalline Sodium Aluminosilicates," J. of the Chemical Society, May 1952. pp. 1561–1571.*
JCPDS Card No's 20–379, 20–743, 25–776, 25–1499, 25–1500, 30–1170, 31–1272, 34–176, 35–479, 35–653, 38–513, 38–514, 38–515 and 45–1373, no dates or authors available.*
Barrer, Hydrothermal Chemistry of Zeolites, p. 307.*
Patent Abstracts of Japan, vol. 18, No. 276 (May 26, 1994).
Patent Abstracts of Japan, vol. 95, No. 11 (Dec. 26, 1995).
Patent Abstracts of Japan, vol. 14, No. 397 (Aug. 28, 1990).

* cited by examiner

*Primary Examiner*—David Sample
(74) *Attorney, Agent, or Firm*—Birch, Stewart, Kolasch & Birch, LLP

(57) ABSTRACT

An aluminosilicate in an acicular form, a platy form, or a columnar form and having the composition represented by $aM_2O \cdot bAl_2O_3 \cdot cSiO_2 \cdot dR_mA_n \cdot yH_2O$, wherein M is at least one of Na and K; R is one or more elements selected from the group consisting of Na, K, Ca and Mg; A is one or more members selected from the group consisting of $CO_3$, $SO_4$, $NO_3$, OH and Cl; a is from 1 to 6; b is from 2 to 8; c is from 2 to 12; d is from 0 to 4; m is from 1 to 2; n is from 1 to 3; and y is from 0 to 32; a polishing agent including the aluminosilicate; and a detergent composition including the aluminosilicate.

16 Claims, 4 Drawing Sheets

ALUMINOSILICATE

This application is the national phase under 35 U.S.C. §371 of PCT International Application No. PCT/JP98/04852 which has an International filing date of Oct. 26, 1998, which designated the United States of America.

TECHNICAL FIELD

The present invention relates to an aluminosilicate. More specifically, the present invention relates to an aluminosilicate which can be used for detergent builders, oil-absorbing agents, polishing agents, scrubbing agent, adsorbents, filter media, fillers, or the like.

BACKGROUND ART

Since aluminosilicates have high stability and are inexpensive, they are widely used in such applications as detergent builders, polishing agents for toothpaste, fillers for paper, and adsorbents. A great majority of the aluminosilicates are zeolite based on $Na_2O$—$SiO_2$—$Al_2O_3$. However, since the zeolite has the shape of sharp-edged cubes with smooth surfaces owing to the tendency to form cubic crystals, there is a problem in that it is likely to damage material upon polishing even though its polishing effect is high. In addition, when the zeolite is filled into a resin, or the like, the surface becomes slidable so that there is a problem in that the mechanical strength of the resin is lowered. Further, even when the zeolite is used for adsorbents, oil-absorbing agents, and the like, the void fraction of the particles themselves is small, so that there is a problem in that the aluminosilicate must be used in large amounts.

Recently, various processes have been proposed for solving the above problems. Japanese Patent No. 2,618,021 discloses a spherical zeolite powder. However, in this patent publication, although the zeolite powder has excellent dispersibility owing to its spherical shape, the zeolite powder has excellent surface slidability and small voids, so that it cannot suitably be used for fillers, adsorbents, or the like. In addition, Japanese Patent No. 2,555,475 discloses porous, inorganic microspheres. Even in this case, however, their surfaces are slidable, so that the microspheres cannot be suitably used for polishing agents, fillers, or the like.

Accordingly, in view of the problems in the prior art described above, an object of the present invention is to provide a porous aluminosilicate which is useful in a wide range of applications such as detergent builders, oil-absorbing agents, polishing agents, scrubbing agent, adsorbents, filter media, fillers, or the like having high polishing ability, low damage to the contacted material, excellent adsorption and dispersibility, and an increased mechanical strength of the filled material when used for fillers.

These and other objects of the present invention will be apparent from the following description.

DISCLOSURE OF THE INVENTION

In sum, the present invention pertains to an aluminosilicate in an acicular form, a platy form, or a columnar form and having the composition represented by:

wherein M is at least one of Na and K; R is one or more elements selected from the group consisting of Na, K, Ca and Mg; A is one or more members selected from the group consisting of $CO_3$, $SO_4$, $NO_3$, OH and Cl; a is from 1 to 6; b is from 2 to 8; c is from 2 to 12; d is from 0 to 4; m is from 1 to 2; n is from 1 to 3; and y is from 0 to 32, and their use.

BEST MODE FOR CARRYING OUT THE INVENTION

Figure 1:
FIG. 1 is a photomicrograph showing the shapes of clusters of the aluminosilicate prepared in Example 1.

As described above, the aluminosilicate of the present invention in an acicular form, a platy form, or a columnar form has the composition represented by:

wherein M is at least one of Na and K; R is one or more elements selected from the group consisting of Na, K, Ca and Mg; A is one or more members selected from the group consisting of $CO_3$, $SO_4$, $NO_3$, OH and Cl; a is from 1 to 6; b is from 2 to 8; c is from 2 to 12; d is from 0 to 4; m is from 1 to 2; n is from 1 to 3; and y is from 0 to 32.

In the aluminosilicate mentioned above, M is at least one of Na and K, preferably Na. When M is both Na and K, $aM_2O$ is expressed as $a_1Na_2O.a_2K_2O$, wherein $a_1+a_2=a$.

In the aluminosilicate mentioned above, R is one or more elements selected from the group consisting of Na, K, Ca and Mg, with a preference given to Na.

In the aluminosilicate mentioned above, A is one or more members selected from the group consisting of $CO_3$, $SO_4$, $NO_3$, OH and Cl, with a preference given to $CO_3$ and $NO_3$, more preferably $NO_3$.

In the aluminosilicate having the above composition, a is from 1 to 6; b is from 2 to 8;, c is from 2 to 12; d is from 0 to 4; m is from 1 to 2; n is from 1 to 3; and y is from 0 to 32.

The aluminosilicate of the present invention is in an acicular, platy, or columnar form. Here, the acicular crystals are those having a thickness of 500 nm or less, and a length with an aspect ratio of 2.0 or more to the thickness; the platy crystals are those having a thickness of 300 nm or less, and the platy size with an aspect ratio of 2.0 or more to the thickness; and columnar crystals are those having a thickness of 50 nm or more, and a length with an aspect ratio of 1.0 or more and less than 2.0 to the thickness. The aluminosilicate described above can be obtained as clusters of acicular crystals, platy crystals, or columnar crystals depending upon the production conditions. Incidentally, the aluminosilicate may preferably have shapes, including clusters of a spherical shape, a tetrapod-like shape, or masses. Alternatively, secondary agglomeration thereof cain be also used. In addition, the porosity of the aluminosilicate of the present invention is crucial from the viewpoints of its oil-absorbing ability and adsorption property, and it is desired that the void fraction in the clusters is 20% by volume or more, preferably 30% by volume or more, and that the void fraction is 90% by volume or less. The void fraction is calculated from the cross-sectional shape of the clusters.

When the shape of the aluminosilicate is spherical, those having a main X-ray diffraction peak at d=0.365±0.015 nm are preferable from the viewpoint of maintaining a spherical form when clustered. Here, the term "main X-ray diffraction peak" refers to the most intensive X-ray diffraction peak or an X-ray diffraction peak having a diffraction intensity of 20% or more to the intensity of the most intensive X-ray diffraction peak.

It is desired that the aluminosilicate has one or more cancrinite-like X-ray diffraction patterns selected from the group consisting of JCPDS (Joint Committee on Powder Diffraction Standards) Nos. 20-379, 20-743, 25-776, 25-1499, 25-1500, 30-1170, 31-1272, 34-176, 35-479, 35-653, 38-513, 38-514, 38-515, and 45-1373. In particular, highly porous aluminosilicates comprising acicular crystals, platy crystals, or columnar crystals have a cancrinite-like X-ray diffraction pattern of JCPDS No. 38-513, and have a composition wherein a is from 2 to 3; b is 3; c is 6; d is from 1 to 2; R is Na; m is 1; and n is from 1 to 2.

In addition, it is desired that the aluminosilicate of the present invention has an average particle size of from 0.1 to 500 $\mu$m, preferably from 1 to 100 $\mu$m.

A process for preparing the aluminosilicate of the present invention is not limited to specified ones. Examples thereof include a process comprising reacting an Al compound and an Si compound in in alkali solution in the presence of $CO_3^{2-}$, $SO_4^{2-}$, $NO_3^-$, $Cl^-$, or the like.

Examples of starting materials for $CO_3^{2-}$ include carbon dioxide, sodium carbonate, potassium carbonate, potassium sodium carbonate, calcium carbonate, magnesium carbonate, and the like. Examples of starting materials for $SO_4^{2-}$ include sodium sulfate, potassium sulfate, potassium sodium sulfate, and the like. Examples of starting materials for $NO_{3-}$ include nitric acid, sodium nitrate, potassium nitrate, and the like. Examples of starting materials for $Cl^-$ include sodium chloride, potassium chloride, and the like.

Examples of the Al compound include aluminum oxide, aluminum hydroxide, sodium aluminate, and the like. Examples of the Si compound include silica sand, silica rock, water glass, sodium silicate, and the like. Alternatively, examples of starting materials for both the Al compounds and the Si compounds include clay minerals, such as kaolin, montmorillonite, bentonite, mica, and talc; aluminosilicate minerals, such as mullite, and the like.

Examples of alkali sources for the alkali solution include oxides, such as sodium oxides and potassium oxide; hydroxides, such as sodium hydroxide and potassium hydroxide; carbonates, such as sodium carbonate, potassium carbonate, and potassium sodium carbonate; and hydrogencarbonates, such as sodium hydrogencarbonate and potassium hydrogencarbonate. There can be added, as occasion demands, oxides, such as calcium oxide and magnesium oxide; hydroxides, such as calcium hydroxide and magnesium hydroxide; carbonates, such as calcium carbonate, magnesium carbonate, and dolomite; and hydrogencarbonates, such as calcium hydrogencarbonate and magnesium hydrogencarbonate.

The aluminosilicate of the present invention can be prepared by blending the various compounds mentioned above in a given proportion. The bending proportion is appropriately determined depending upon the composition of the resulting desired aluminosilicate. Specifically, in a case where each of the starting materials is represented by the formulas $aM_2O$, $bAl_2O_3$, $cSiO_2$, and $dR'_mA_n$, wherein KOH, for instance, is calculated as $K_2O$, and NaOH is calculated as $Na_2O$, it is desired that the blending proportion of the starting materials is such that b/c is from 0.01 to 10, a/c is from 0.01 to 100, and d/c is from 0.01 to 100.

In addition, it is desired that the reaction temperature upon preparation of the aluminosilicate of the present invention is 15° C. or more, preferably 60° C. or more, more preferably 80° C. or more, from the viewpoints of increasing the crystallinity of the aluminosilicate and stabilizing the shape of the aluminosilicate, and that the reaction temperature is 300° C. or less, preferably 150° C. or less, more preferably 130° C. or less:, from the viewpoints of reducing chemical loads and pressure-withstanding loads to the reaction vessel. Also, it is desired that the reaction time is 2 hours or more, preferably 8 hours or more from the viewpoint of completely carrying out the crystallization reaction.

For instance, it is desirable to react a mixed solution containing an Al compound, an Si compound, and an $R'_mA_n$ compound, wherein R' is one or more element selected from the group consisting of H, Na, K, Ca and Mg; and A, m and n are the same as defined above;, at a temperature of from 150° to 300° C. Incidentally, in this preferred embodiment, it is desired that the Al compound is sodium aluminate, that the Si compound is sodium silicate, and that the $R'_mA_n$ compound is one or more compounds selected from nitric acid, sodium nitrate and sodium hydroxide. In addition, it is desired that the concentration of the solid components in the aluminosilicate having the above composition during the reaction is from 0.1 to 50% by weight.

The oil-absorbing ability of the aluminosilicate of the present invention is essential for supporting liquid surfactants, chemicals, food, perfume, or the like, and the oil-absorbing ability is preferably 0.5 ml/g or more, more preferably 0.8 ml/g or more, still more preferably 1.0 ml/g or more, from the viewpoint of preventing bleeding of the liquid components.

Here, the oil-absorbing ability is measured by a method according to JIS5101, pigment test method (oil-absorbing ability), where the substance to be absorbed is measured with a nonionic surfactant in place of linseed oil.

The aluminosilicate of the present invention has high polishing ability, so that it has excellent adsorption and dispersibility without damaging the contacted material, and has a property that when used as a filler, the filled material has an increased mechanical strength.

As to the form of the aluminosilicate of the present invention, the aluminosilicate is suitably used in the form of powder from the aspect of giving high dispersibility. In addition, the aluminosilicate of the present invention may be used by blending other inorganic powders, organic powders, metal powders or the like, and as occasion demands, the aluminosilicate may be used as a molded product.

The applications of the aluminosilicate of the present invention include detergent builders, oil-absorbing agents, polishing agents, scrubbing agents, adsorbents, filter media, filler, and the like. Concrete applications include, for instance, polishing agents for detergents for tableware, teeth, metals, plastics, glass, paints, plating and resins; carrier; for dyes and pigments; adsorbents for sterilizer, and insecticidal agents; adsorbents for various perfumes; adsorbents for various gases; fillers for pocket warmers; oil-absorbing carriers; filter aids; fillers to papers, plastics, resins, and the like; carriers for dyes and pigments; extenders for cosmetics; ion exchangers; water treatment agents; various bacteria carriers for water treatment; desiccants for high-temperature gases, and the like, among which polishing agents are particularly preferred.

In addition, the aluminosilicate of the present invention may be used together with a surfactant, such as an anionic surfactant, an amphoteric surfactant, or a nonionic surfactant, in an amount of about 1 to about 50% by weight to the aluminosilicate, to prepare a detergent composition.

Examples of the anionic surfactant include salts of sulfuric acid esters of higher alcohols or ethoxylated products thereof; alkylbenzenesulfonates; paraffinsulfonates; α-olefinsulfonates; salts of α-sulfofatty acids; salts of alkyl esters of α-sulfofatty acids; salts of α-sulfofatty acids, and the like. Here, salts are preferably alkali metal salts, such as sodium salts and potassium salts.

Examples of the amphoteric surfactant include betaine-type amphoteric surfactants, such as carboxybetaine, sulfobetaine, and amidebetaine amphoteric surfactants; alkyldimethylamine oxides, and the like.

Examples of the nonionic surfactant include ethylene oxide adducts of higher alcohols; ethylene oxide/propylene oxide adducts of higher alcohols; fatty acid alkanolamides; alkyl polyglycosides, and the like.

The applications of the detergent composition are not limited to specified ones. Examples of the applications include clothes detergents, dishwash detergents, house cleaning detergents, car washing detergents, toothpastes, body detergents, and metal detergents. In particular, the detergent composition is preferably used as car washing detergents having polishing ability.

Next, the aluminosilicate of the present invention will be described in further detail on the basis of the following working examples, without intending to limit the scope or spirit of the present invention thereto.

EXAMPLE 1

In a solution prepared by dissolving 1120 g of potassium hydroxide and 850 g of sodium nitrate in 5000 ml of ion-exchanged water was mixed and dispersed 50 g of kaolin, and the resulting mixture was reacted at 80° C. with stirring for 24 hours. After termination of reaction, the resulting aluminosilicate was washed, filtered and dried, to give a powder of the aluminosilicate. The resulting aluminosilicate was formed into a porous sphere in which the platy crystals were clustered as shown in FIG. 1.

In a beaker was weighed 2 g of the resulting aluminosilicate, and an oil, polyoxyethylene lauryl ether, was added dropwise with stirring with a glass rod. The oil-absorbing ability was obtained from the amount of the polyoxyethylene lauryl ether required for adhering the oil-absorbed aluminosilicate in masses, and the oil-absorbing ability was found to be 1.3 ml/g.

The powder of the resulting aluminosilicate was analyzed by X-ray diffraction using an X-ray diffraction analyzer "RAD-C" (manufactured by Rigaku, CuKα). As a result, the powder had an intensive diffraction peak at d=0.367 nm, which corresponded to JCPDS No. 38-513. The approximate composition of the aluminosilicate was $K_2O.2Na_2O.3Al_2O_3.6SiO_2.2NaNO_3.6H_2O$.

EXAMPLE 2

Figure 2:
FIG. 2 is a photomicrograph showing the shapes of clusters of the aluminosilicate prepared in Example 2.

In a solution prepared by dissolving 800 g of sodium hydroxide and 850 g of sodium carbonate in 5000 ml of ion-exchanged water was mixed and dispersed 50 g of kaolin. The same procedures as in Example 1 were carried out to give a powder of the aluminosilicate. The resulting aluminosilicate was formed into a porous sphere in which the columnar crystals were clustered as shown in FIG. 2.

The oil-absorbing ability was obtained in the same manner as in Example 1, and it was found to be 0.55 ml/g.

In addition, the powder of the resulting aluminosilicate was analyzed by X-ray diffraction in the same manner as in Example 1. As a result, the powder had an intensive diffraction peak at d=0.367 nm, which corresponded to JCPDS No. 38-513. The approximate composition of the aluminosilicate was $3Na_2O.3Al_2O_3.6SiO_2.Na_2CO_3.2H_2O$.

EXAMPLE 3

Figure 3:
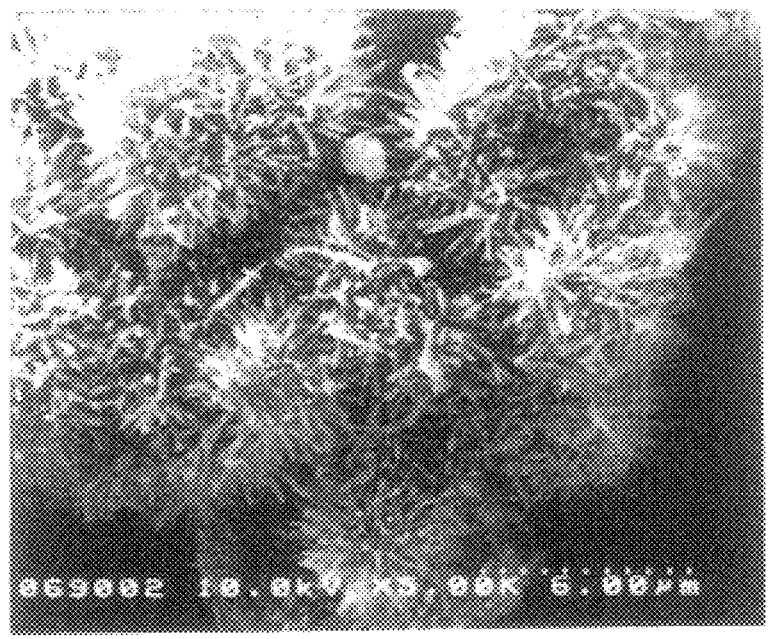
FIG. 3 is a photomicrograph showing the shapes of clusters of the aluminosilicate prepared in Example 3.

In a solution prepared by dissolving 860 g of sodium aluminate, 1450 g of sodium hydroxide, and 1530 g of sodium nitrate in 27000 ml of ion-exchanged water was added and mixed No. 3 sodium silicate ($Na_2O$: 9.7% by weight, $SiO_2$: 29.7% by weight, $H_2O$: 60.6% by weight). The same procedures as in Example 1 were carried out to give a powder of the aluminosilicate. The resulting aluminosilicate was formed into a porous sphere in which the acicular crystals were clustered as shown in FIG. 3.

Figure 5:
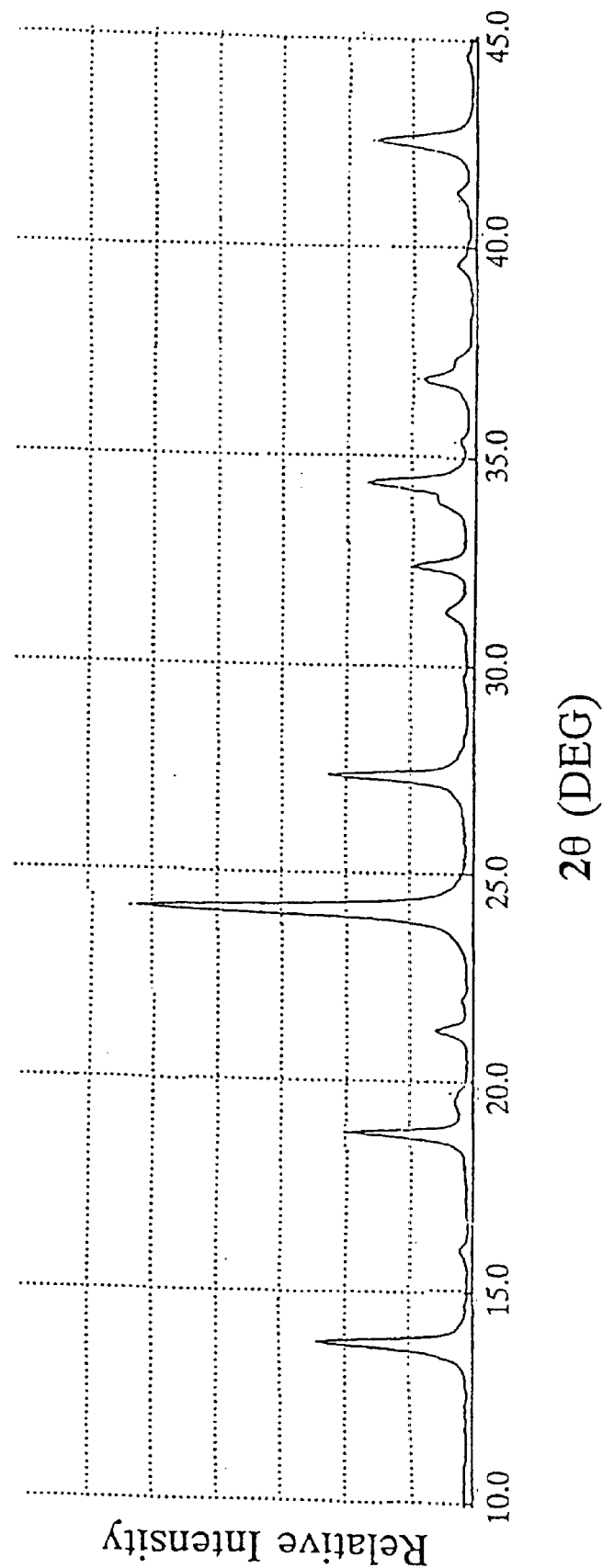
FIG. 5 is a chart showing an X-ray diffraction pattern of the aluminosilicate prepared in Example 3.

The oil-absorbing ability was obtained in the same manner as in Example 1, and it was found to be 1.8 ml/g. In addition, the powder of the resulting aluminosilicate was analyzed by X-ray diffraction in the same manner as in Example 1. As a result, the powder had an intensive diffraction peak at d=0.366 nm, which corresponded to JCPDS No. 38-513. The resulting X-ray diffraction pattern is shown in FIG. 5. The approximate composition of the aluminosilicate was $3Na_2O.3Al_2O_3.6SiO_2.NaNO_3.4H_2O$.

EXAMPLE 4

The following properties as a polishing agent were evaluated for each of the aluminosilicates prepared in Examples 1 to 3.

Figure 4:
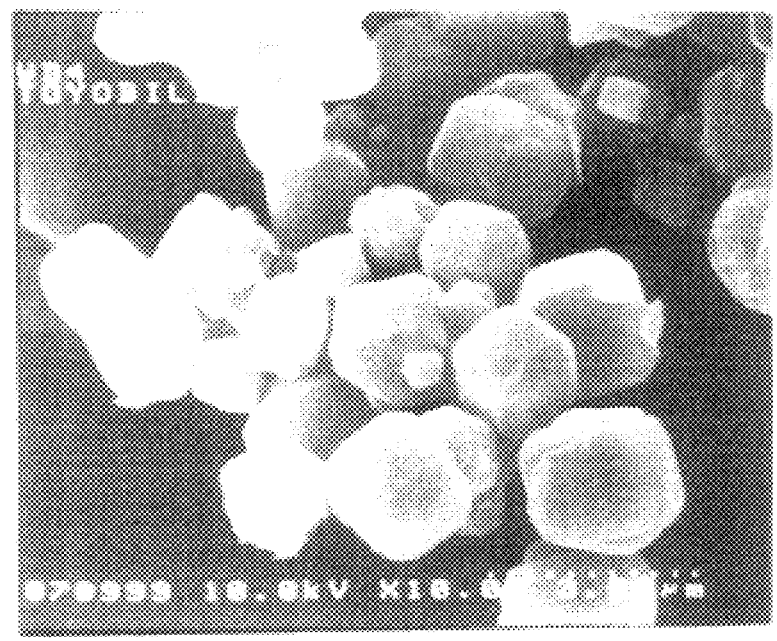
FIG. 4 is a photomicrograph showing the shapes of the 4A zeolite powder used as Comparative Example.

Each of dispersion which was prepared by dispersing the each of the powder of the aluminosilicates prepared in Examples 1 to 3 and 4A zeolite powder used as Comparative Example, the 4A zeolite powder being non-agglomerated, cubic crystals having the form shown in FIG. 4, in a water:glycerol solvent at a weight ratio of 1:1, each of the aluminosilicates being added so as to have a concentration of 10% by weight, was poured between two acrylic plates having dimensions of 10 cm×10 cm×0.5 cm. One of the acrylic plates was fixed, while the other acrylic plate was reciprocally slid for 100 times under a load of 5 kgf, and thereafter the wear and the damages of the fixed acrylic plate were evaluated.

The results are shown in Table 1. In Table 1, when evaluating wear, "excel." means that the amount of polish as expressed by the weight loss of the acrylic plate is 0.1 g or more per one acrylic plate, and "good" means that the amount of polish as expressed by the weight loss of the acrylic plate is from 0.01 to 0.1 g per one acrylic plate. When evaluating damages, "much damages" means that much polishing damages are present on the acrylic plate, thereby showing a ground glassy state; "little damages" means that although there are some polishing damages on the acrylic plate, the acrylic plate maintains transparency; and "no damages" means that the polished portion of the acrylic plate has the same level of transparency as the non-polished portion of the acrylic plate.

TABLE 1

| Powder Used | Wear | Damages |
| --- | --- | --- |
| Example 1 | Good | No Damages |
| Example 2 | Excel. | Little Damages |

TABLE 1-continued

| Powder Used | Wear | Damages |
|---|---|---|
| Example 3 | Good | No Damages |
| Comparative Example | Good | Much Damages |

The aluminosilicates prepared in Examples 1 to 3 had high polishing ability, giving no damages to the contacted acrylic plate. From the above, these aluminosilicates are highly useful for polishing agents for glass, metal surfaces, resins, painting surfaces, plating surfaces, teeth, or the like.

EXAMPLE 5

The aluminosilicate prepared in. Example 3 was evaluated with respect to steam trapping ability by the following method.

Specifically, each of 100 g of the powder of the aluminosilicate prepared in Example 3 and 100 g of the 4A zeolite powder used as Comparative Example was placed in a stainless vat, and the powder was Kept standing in an environment of 50° C. and relative humidity of 80% for 5 to 60 minutes, and the amount of weight increase with the passage of time was measured to evaluate the steam trapping ability. The results are shown in Table 2.

TABLE 2

| Amount of Steam Trapped with Passage of Time (% by wt.) | Example 3 | Comparative Example |
|---|---|---|
| After 5 minutes | 2.8% | 0.4% |
| After 10 minutes | 3.3% | 0.3% |
| After 60 minutes | 5.8% | -0.4% |

The powder of the aluminosilicate prepared in Example 3 trapped steam even under high-temperature conditions, thereby showing excellent steam trapping ability. It is clear from the above that the aluminosilicate of Example 3 is highly useful as a desiccant for high-temperature gases.

EXAMPLE 6

The aluminosilicates prepared In Examples 1 and 3 were evaluated with respect to oil-absorbing ability by the following method.

Each of the powders of the aluminosilicates prepared in Examples 1 and 3 and the 4A zeolite powder used as Comparative Example was added as a 3surfactant carrier to a nonionic surfactant-based clothes powder detergent in an amount of 15% by weight, and the resulting composition was kept standing on a filter paper. The composition was stored at room temperature for six months, and the bleeding conditions of the nonionic surfactant-based clothes powder detergent were then observed. A typical composition of the used clothes powdery detergent were as follows: 30% by weight of zeolite powder, 20% by weight of sodium carbonate, 10% by weight of No. 1 powdery sodium silicate, 20% by weight of polyoxyethylene lauryl ether, 5% by weight of sodium sulfate, and as an oil-absorbing carrier, 15% by weight of the powder of the resulting aluminosilicates prepared in each of Examples 1 and 3, or the 4A zeolite powder used as Comparative Example.

As a result, when the 4A zeolite powder of Comparative Example was used as a carrier, a large amount of bleeding was found on the filter paper. By contrast, when each of the powders of Examples 1 and 3 was used, substantially no bleeding was found in each of the cases, thereby showing high oil-absorbing ability.

EXAMPLE 7

The aluminosilicates prepared in Examples 1 and 3 were evaluated with respect to dispersibility by the following method.

In water was dispersed each of the powder of the aluminosilicates prepared in Examples 1 and 3 and the 4A zeolite powder used as Comparative Example, so as to have a concentration of 20% by weight. Each of the resulting dispersion was kept standing at room temperature for one month. Thereafter, with shaking and stirring, the re-dispersibility was evaluated.

As a result, it was found that although the powders prepared in Examples 1 and 3 were in the state of sedimentation after being kept standing, these powders were readily re-dispersed by shaking and stirring the mixture, thereby showing excellent dispersibility. On the other hand, the 4A zeolite powder of Comparative Example became a hard sedimentation after being kept standing, so that almost none of which were re-dispersed even with shaking and stirring.

EXAMPLE 8

The aluminosilicate prepared in Example 3 was evaluated with respect to their property as a filler by the following method.

Each of the powder of the aluminosilicate prepared in Example 3 and the 4A zeolite powder used as Comparative Example was kneaded at 170° C. in an amount of 2% by weight or 4% by weight, for each powder into an acrylic resin "ACRYPET" (manufactured by Mitsubishi Rayon Co., Ltd.), and a molded plate of 10 cm×10 cm×2 mm was prepared from the resulting mixture. The strength of each of the resulting molded plates was compared. As a result, it was found that those kneaded with 2% by weight and 4% by weight, respectively, of the powder of Example 3 showed improvements in the bending strength of about 20 to 35%, so that the mechanical strength of the filled material was also increased. However, those in which the powder of Comparative Example was kneaded showed almost no improvements or rather a slight decrease in the mechanical strength.

EXAMPLE 9

Figure 6:
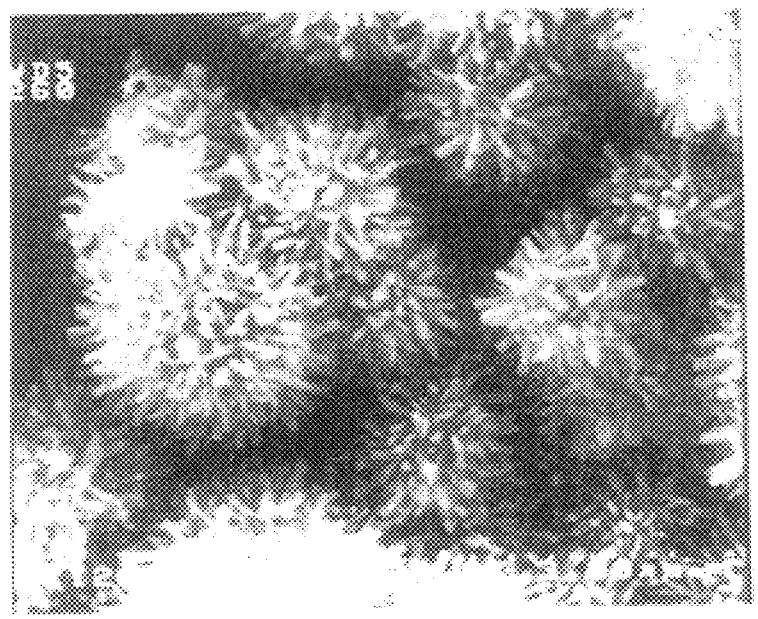
FIG. 6 is a photomicrograph showing the shapes of clusters of the aluminosilicate prepared in Example 9.

In a solution prepared by dissolving 94 g of sodium hydroxide in 1000 ml of ion-exchanged water, and further adding and mixing 130 g of 61% nitric acid and 124 g of a sodium aluminate solution ($Na_2O$: 20.31% by weight; $Al_2O_3$: 25.82% by weight; $H_2O$: 53.87% by weight) was added and mixed 127 g of water glass ($Na_2O$: 9.7% by weight; $SiO_2$: 29.7% by weight; $H_2O$: 60.6% by weight). The resulting mixture was reacted at 100° C. for 15 hours. After the termination of reaction, the powder of the aluminosilicate was prepared in the same manner as in Example 1. The resulting aluminosilicate was formed into a porous sphere in which the acicular crystals were clustered as shown in FIG. 6. Incidentally, the approximate composition was substantially the same as that of Example 3. As a result of X-ray diffraction analysis, it corresponded to JCPDS No. 38-513.

EXAMPLE 10

Figure 7:
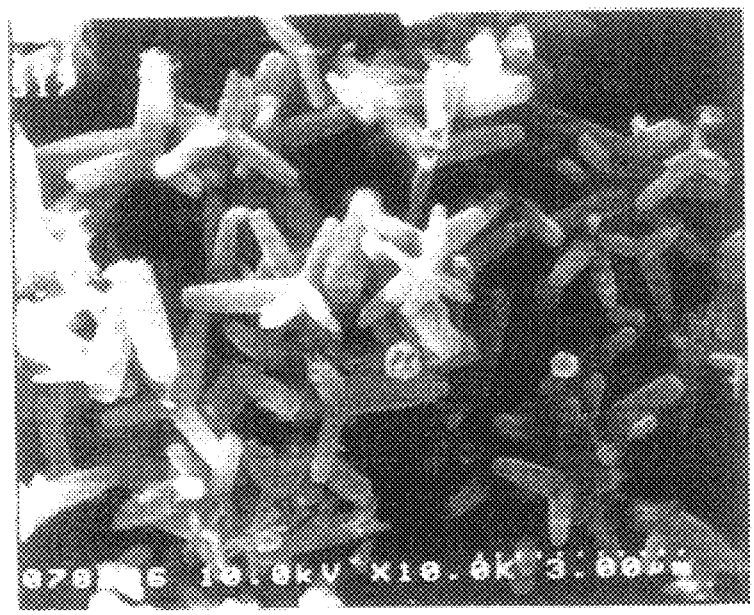
FIG. 7 is a photomicrograph showing the shapes of clusters of the aluminosilicate prepared in Example 10.

In a solution prepared by dissolving 47 g of sodium hydroxide in 1000 ml of ion-exchanged. water, and further adding and mixing 73 g of a sodium aluminate solution (Na₂O: 20.31% by weight; Al₂O₃: 25.82% by weight; H₂O: 53.87% by weight) was added and mixed 119 g of water glass (Na₂O: 9.7% by weight; SiO₂: 29.7% by weight; H₂O: 60.6% by weight). The resulting mixture was reacted at 100° C. for 2 hours. Thereafter, to the above reaction mixture was additionally added a solution prepared by dissolving 15 g of sodium hydroxide in 50 ml of ion-exchanged water, and further adding and mixing 57 g of 61% nitric acid. The resulting mixture was then further reacted at 100° C. for 10 hours. After the termination of reaction, the powder of the aluminosilicate was prepared in the same manner as in Example 1. The resulting aluminosilicate was formed into a tetrapod-like form, into which the columnar crystals were grown as shown in FIG. 7. Incidentally, the approximate composition of the aluminosilicate was 3Na₂O.3Al₂O₃.7SiO₂.2NaNO₃.4H₂O. As a result of X-ray diffraction analysis, it corresponded to JCPDS No. 38-513.

It is clear from the results in Examples that the aluminosilicate of the present invention has excellent oil-absorbing ability, and high polishing ability without damaging of the contacted material, and excellent steam trapping ability, oil-absorbing strength, re-dispersibility, so that when used as a filler the resulting filled material has an increased mechanical strength.

Industrial Applicability

Since the aluminosilicate of the present invention comprises clusters of acicular crystals, platy-crystals, or columnar crystals, the aluminosilicate has high polishing ability without damaging 1the contacted materials, and excellent adsorption and dispersibility, so that an effect of increasing the mechanical strength of the filled materials when used as a filler can be exhibited.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An aluminosilicate in an acicular form, a platy form, or a columnar form and having the composition represented by:

$$aM_2O \cdot bAl_2O_3 \cdot cSiO_2 \cdot dR_mA_n \cdot yH_2O,$$

where M is at least one of Na and K; R is one or more elements selected from the group consisting of Na, K, Ca and Mg; A is NO₃; a is from 1 to 6; b is from 2 to 8; c is from 2 to 12; d is greater than 0 to 4; m is from 1 to 2; n is from 1 to 3; and y is from 0 to 32.

2. The aluminosilicate according to claim 1, wherein the aluminosilicate has a main X-ray diffraction peak at d=0.365±0.015 nm.

3. The aluminosilicate according to claim 1 or 2, wherein the aluminosilicate has one or more X-ray diffraction patterns selected from the group consisting of JCPDS Nos. 20-379, 20-743, 25-776, 25-1499, 25-1500, 30-1170, 31-1272, 34-176, 35-479, 35-653, 38-513, 38-514, 38-515, and 45-1373.

4. The aluminosilicate according to claim 1 or 2, wherein a is from 2 to 3; b is 3; c is 6; d is from 1 to 2; R is Na; m is 1; and n is 1.

5. The aluminosilicate according to claim 1 or 2, wherein the aluminosilicate has an X-ray diffraction pattern of JCPDS No. 38-513.

6. The aluminosilicate according to claim 1, wherein M is Na.

7. The aluminosilicate according to claim 1, wherein R is Na.

8. The aluminosilicate according to claim 1, wherein the aluminosilicate has crystals in the acicular form, having a thickness of 500 nm or less and a length with an aspect ratio of 2.0 or more to the thickness.

9. A polishing agent comprising the aluminosilicate as defined in claim 1 or 2.

10. A detergent composition comprising the aluminosilicate as defined in claim 1 or 2.

11. The aluminosilicate according to claim 1, wherein the aluminosilicate has crystals in a platy form, wherein the platy crystals have a thickness of 300 nm or less and the platy size has an aspect ratio of 2.0 or more to the thickness.

12. The aluminosilicate according to claim 1, wherein the aluminosilicate has crystals in the columnar form, wherein the columnar crystals have a thickness of 50 nm or more and a length with an aspect ratio of 1.0 or more and less than 2.0 to the thickness.

13. The aluminosilicate according to claim 1, wherein the aluminosilicate is in the form of crystals which are clustered and have a void fraction in the clusters of 20% to 90% by volume.

14. The aluminosilicate according to claim 1, wherein the aluminosilicate has a particle size of 0.1 to 500 microns.

15. The aluminosilicate according to claim 1, wherein the aluminosilicate is prepared in a process comprising combining starting materials represented by $cSiO_2$ and $dR_mA_n$ in the ratio of d/c of 0.01 to 100.

16. The aluminosilicate according to claim 1, wherein the aluminosilicate has an approximate composition selected from the group consisting of $K_2O \cdot 2Na_2O \cdot 3Al_2O_3 \cdot 6SiO_2 \cdot 2NaNO_3 \cdot 6H_2O$, $3Na_2O \cdot 3Al_2O_3 \cdot 6SiO_2 \cdot NaNO_3 \cdot 4H_2O$, and $3Na_2O \cdot 3Al_2O_3 \cdot 7SiO_2 \cdot 2NaNO_3 \cdot 4H_2O$.

* * * * *